(12) United States Patent
Peters et al.

(10) Patent No.: US 11,937,832 B2
(45) Date of Patent: Mar. 26, 2024

(54) DRILL BIT, DRILL KIT AND METHOD FOR DRILLING A CAVITY OR A RECESS INTO A SKULL

(71) Applicant: Oticon Medical A/S, Smørum (DK)

(72) Inventors: Hanna Peters, Askim (SE); Emelie Lager, Askim (SE); Anton Hedström, Askim (SE); Martin Johansson, Askim (SE); Thomas Eriksson, Askim (SE)

(73) Assignee: Oticon Medical A/S, Smørum (DK)

( * ) Notice: Subject to any disclaimer, the term of this patent is extended or adjusted under 35 U.S.C. 154(b) by 287 days.

(21) Appl. No.: 17/369,312

(22) Filed: Jul. 7, 2021

(65) Prior Publication Data

US 2022/0008088 A1 Jan. 13, 2022

(30) Foreign Application Priority Data

Jul. 8, 2020 (EP) .................................. 20184691

(51) Int. Cl.
| | | |
|---|---|---|
| A61B 17/16 | (2006.01) | |
| A61B 17/17 | (2006.01) | |
| A61B 17/56 | (2006.01) | |

(52) U.S. Cl.
CPC ...... *A61B 17/1695* (2013.01); *A61B 17/1615* (2013.01); *A61B 17/1739* (2013.01); *A61B 2017/564* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1662; A61B 17/1673; A61B 17/1679; A61B 17/1695
See application file for complete search history.

(56) References Cited

U.S. PATENT DOCUMENTS

| | | | | |
|---|---|---|---|---|
| 2014/0220508 | A1* | 8/2014 | Scalise ................. | A61C 8/0089 433/173 |
| 2015/0025559 | A1 | 1/2015 | Kulas et al. | |
| 2018/0168772 | A1* | 6/2018 | Abboud ............... | A61C 8/0089 |

(Continued)

FOREIGN PATENT DOCUMENTS

| | | | | | |
|---|---|---|---|---|---|
| CN | 108495592 | A | * | 9/2018 | ......... A61B 17/1615 |
| CN | 113993051 | A | * | 1/2022 | ......... A61B 17/1615 |
| EP | 3936064 | A1 | * | 1/2022 | ......... A61B 17/1615 |

*Primary Examiner* — Eric S Gibson
(74) *Attorney, Agent, or Firm* — Birch, Stewart, Kolasch & Birch, LLP

(57) ABSTRACT

A drill bit for drilling a cavity or a recess into a skull, wherein the cavity or the recess is configured to receive an implantable fixture screw unit of a hearing aid system, is disclosed. The drill bit includes a first part including a drill tip with a first drill diameter, wherein the drill tip comprises a tip angle of between 137 degrees to 143 degrees along a longitudinal axis of the drill bit and wherein the drill tip comprises a back rake angle of between −1 degree and +1 degree, in particular a back rake angle of substantially 0 degrees, a second part including a plurality of flute blades with a second drill diameter, wherein the second drill diameter is greater that the first drill diameter, and a transition part which is arranged between the first part and the second part and along the longitudinal axis, wherein the transition part includes a body clearance.

20 Claims, 7 Drawing Sheets

(56) References Cited

U.S. PATENT DOCUMENTS

2019/0029695 A1* 1/2019 Huwais ................ A61C 8/0089
2019/0029696 A1* 1/2019 Feldmann .......... A61B 17/1615
2022/0008088 A1* 1/2022 Peters ................ A61B 17/1695

* cited by examiner

DRILL BIT, DRILL KIT AND METHOD FOR DRILLING A CAVITY OR A RECESS INTO A SKULL

FIELD OF THE DISCLOSURE

The present disclosure relates to the field of drill bits, drill kits and methods for drilling. More particularly, the disclosure relates to a drill bit, a drill kit and a method for drilling a cavity or a recess into a skull, wherein the cavity or the recess is configured to receive an implantable fixture screw unit of a hearing aid system.

BACKGROUND

Medical implants such as bone anchored hearing aid systems are applied for the rehabilitation of patients suffering from hearing losses for which traditional hearing aids are insufficient. A typical bone anchored hearing aid system comprises an external hearing aid provided with a vibrating transducer connected to a skin-penetrating abutment through a coupling. The abutment may have an interconnection to an implantable fixture screw unit anchored in the skull bone. The implantable fixture is typically made of titanium and may be provided with a flange to prevent the fixture from being pushed through the skull bone when exposed to a sudden accidental impact.

The abutment penetrates the skin and the subcutaneous tissue in order to establish a direct coupling (direct bone conduction) from a hearing aid processor to the skull bone.

The methods for installing bone anchored hearing aid implant systems are moving towards minimally invasive methods that can be performed quickly in order to minimize intra- and post-operative problems, to achieve a predictable outcome, and to achieve better cosmetic results.

However, the existing incision techniques are rather complicated and require a flap area to be provided by making an incision. Typically, a scalpel is used to make an incision down to the periosteum along a marking of the incision area and to separate the tissue from the underlying periosteum. Further, all subcutaneous tissue in the graft area is separated from the periosteum. Additionally, the subcutaneous tissue needs to be carefully separated from the skin graft, and all hair follicles need to be removed. Furthermore, some level of manual skin thinning typically is required to be performed.

Some attempts have been made to avoid the linear incision techniques to install implants for bone anchored hearing aids. Some of these attempts include punch techniques. The techniques apply a standard biopsy punch that is used to provide a circular incision of 5-12 mm.

These techniques are associated with a number of drawbacks. These drawbacks include the risk of damaging the tissue due to friction, heat and tearing caused by the action of the drill.

The punching techniques apply punching holes larger than 5 mm in order to allow for introducing irrigation fluid (to cool the bone tissue) during the drilling process and also for providing sufficient visibility. These large punch diameters are not optimal for the soft tissue abutment interface. A large circular incision will prolong the healing time and introduce the risk of granulation tissue formation and subsequent infection. Moreover, the skin thickness needs to be determined pre- and/or intra-operatively.

Additionally, it is known to use a minimally invasive Ponto surgery technique in order to install implants for bone anchored hearing aids. Hereby, an incision hole is made by using a biopsy punch. Afterwards the periosteum and soft tissue are removed from the transplantation site. The drilling procedure comprises two different drilling steps. A first drill is used in order to generate a first cavity or recess. Afterwards, a widening drill is used in order to widen the first cavity or recess and to prepare the cavity or recess for the implant for bone anchored hearing aids. By using different drills, the operation surgery time is prolonged and the switching, restarting and realigning of the widening drill may cause adverse consequences for the cavity or recess to be drilled.

Therefore, there is a need to provide a solution that addresses at least some of the above-mentioned problems.

SUMMARY

According to a first exemplary aspect a drill bit for drilling a cavity or a recess into a skull is disclosed. The drill bit may comprise a first part including a drill tip with a first drill diameter, wherein the drill tip comprises a tip angle of between 137 degrees to 143 degrees along a longitudinal axis of the drill bit. A tip angle of between 137 degrees to 143 degrees is advantageous for drilling into the relatively hard skull material. The tip angle of between 137 degrees and 143 degrees enables a sufficient engagement of the cutting lips of the drill tip with the skull material. The first part of the drill bit is the part of the drill bit which is closest to the bone during drilling. The drill tip may include a pointed end interfacing with the bone. Although the term pointed is used, the term pointed includes any known structure, interfacing with the bone at the start of drilling, that facilitates piercing of the bone for creation of a preliminary hole. The drill tip may comprise a back rake angle of between −1 degree and +1 degree, in particular a back rake angle of substantially 0 degrees. The back rake angle describes the angle of the cutting face of the drill tip relative to the skull. A negative back rake angle of the drill tip leads to a slightly duller cutting edge design. Hereby, the tactile feedback while feeding the drill may be increased. Zero rake angle or a positive rake angle leads to a sharper and more pointed drill bit. Thus, cutting forces and power requirements for the drill step may be reduced. The length along the longitudinal axis of the first part may be less than the length along the longitudinal axis of the second part.

The drill bit may further comprise a second part including a plurality of flute blades with a second drill diameter, wherein the second drill diameter is greater than the first drill diameter. By providing a drill bit comprising a first drill diameter and a second drill diameter, wherein the second drill diameter is greater than the first drill diameter, a cavity or a recess for an implantable fixture screw unit of a hearing aid system may be drilled into the skull in one drill step. Hereby, the final osteotomy for an implant may be performed in one step. The drill diameter of the first or the second part of the drill tip may be defined as the maximum diameter along the longitudinal axis of the first or the second part of the drill bit.

The drill bit may further comprise a transition part which is arranged between the first part and the second part and along the longitudinal axis, wherein the transition part includes a body clearance.

According to another aspect, a drill kit comprising a drill bit according to the first exemplary aspect and further comprising a guiding tool is disclosed. The guiding tool may comprise a hollow tube, wherein the diameter of the hollow tube is greater than the second drill diameter. Hereby, the soft tissue may be protected from the drill bit. Additionally, saline or a coolant may be filled in the guiding tool in order to cool during the drilling process. The guiding tool may act as a hard stop for the drilling bit, so that the drill depth can be controlled.

According to yet another aspect, a method for drilling a cavity or a recess into a skull, wherein the cavity or the recess is configured to receive an implantable fixture screw unit of a hearing aid system, is disclosed. The method may comprise applying an incision hole to a bone layer of the skull by using a first tool. The incision hole may be applied by the usage of a punching tool in order to make the incision hole.

The method may further comprise cleaning the incision hole by using a cleaning tool. The step cleaning the cavity or the recess may additionally comprise the removal of the periosteum and soft tissue. The method may further comprise arranging a guiding tool into the cleaned cavity or recess, wherein the guiding tool includes a hollow tube. The method may further comprise applying the drill bit into the hollow tube and drilling the cavity or the recess in a single step. The step drilling the cavity or the recess in a single step may be performed without switching the drill bits. The cavity or the recess has a diameter and depth matching the dimensions of the implant so that the implant may be screwed into the cavity or recess. In an embodiment, the implant includes an implant of a bone anchored hearing aid.

In the following, further exemplary features of all aspects of the present invention will be described in more detail.

A hearing aid system may generally be understood or include a hearing aid (which may also be termed a hearing device, a hearing instrument or a hearing assistance device) that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss. The "hearing aid" may further refer to a device such as a hearable, an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

The hearing aid of the hearing system is adapted to be worn in any known way. This may include arranging a unit of the hearing aid attached to a fixture implanted into the skull bone such as in a Bone Anchored Hearing Aid or arranging a unit of the hearing aid as an entirely or partly implanted unit such as in a Bone Anchored Hearing Aid. The hearing aid may be implemented in one single unit (housing) or in a number of units individually connected to each other.

In an embodiment of the disclosure, each of the plurality of flute blades of the second part of the drill bit may comprise at least one land, wherein the second part comprises parabolic or essentially parallel, in particular cross-section defining, opposing surfaces extending between the lands of the plurality of flute blades. The land of a flute blade may be defined as the outer portion of the flute blade between two adjacent flutes. The parabolic or essentially parallel surfaces of the second part leads to an improved bone chip extraction. Additionally, the total drill work can be reduced so that an efficient removal of bone volume can be provided.

The plurality of the flute blades of the second part may comprise a cutting edge with a thickness of between 0.10 mm to 0.40 mm. Said cutting edge thickness of the plurality of flute blade is beneficial for the cutting efficiency of the drill bit.

A pair of adjacent flute blades may define drill flutes between adjacent flute blades, wherein the thickness of the drill flutes or the flute blades may vary along the drill bit, in particular along the longitudinal axis of the drill bit. This allows for optimizing the thickness distribution of the drill bit regarding the force and torque of the drill bit. The thickness of the drill flutes may vary between 0.8 mm and 1.2 mm.

The second part of the drill bit may include at least two flute blades such as two or three or four or more flute blades along the longitudinal axis of the drill bit.

The second part or the transition part of the drill bit may include a back-rake angle which is either positive or negative. The back rake angle describes the angle of a cutting face relative to a workpiece (e.g. to the skull). A negative back rake angle of the second part or the transition part leads to an increase of tactile feedback while feeding the drill. A positive rake angle leads to a reduction of cutting forces and power requirements. The back rake angle of the flute blades may be within an angle range of between −3 degrees to +3 degrees not including 0 degrees.

The second part of the drill bit may include a helix angle between the longitudinal axis and a direction of the flute blades, in particular a plane of the flute blades, of between 20 degrees to 30 degrees, in particular a helix angle of between 24 degrees and 26 degrees. The second part of the drill bit may also include a helix angle of 25 degrees between the longitudinal axis and the direction of the flute blades along the longitudinal axis. Aforementioned helix angles lead to an increased bone chip removal and are beneficial for the feed rate of the drill bit.

The transition part of the drill bit may include a region with constant diameter along the longitudinal axis. The length of the region with constant diameter along the longitudinal axis may be between 1.05 mm and 1.55 mm. Preferably, the region of constant diameter does not have a cutting edge.

The body clearance of the transition part of the drill bit may include a minimum diameter equal to a diameter of the first part, preferably to a minimum diameter of the first part, and a maximum diameter equal to a diameter of the second part. Hereby, a smooth transition between the first part of the drill bit and the second part of the drill bit may be provided.

The body clearance of the transition part may include a transition angle of 7 degrees to 13 degrees along the longitudinal axis and between a minimum diameter and a maximum diameter of the transition part. The transition angle may be defined as the angle between the plane perpendicular to the longitudinal axis of the drill bit and the body clearance of the transition part of the drill bit. Said transition angle is beneficial for providing a cavity or a recess in a skull with one drill bit in one drilling step.

A first length along the longitudinal axis and between the end of the drill tip and the maximum diameter of the transition part may be between 4.65 mm and 4.75 mm. The drill bit may have a first drill diameter between 3.78 mm and 3.82 mm.

The drill tip may include a cutting edge angle of 7 degrees to 13 degrees. The cutting edge angle may be defined as an angle formed by a flank of the drill tip and a plane perpendicular to the longitudinal axis. Said cutting edge angle provides beneficial strength and rigidity to the cutting edge. The cutting edge angle may also be defined as the clearance angle of the drill tip.

The drill tip may comprise a web thickness of between 0.20 mm to 0.30 mm, especially of between 0.24 mm to 0.26 mm. The web thickness is the thickness of the drill tip in a plane perpendicular to the longitudinal axis. The aforementioned web thickness may be beneficial regarding the needed thrust to apply to the drill bit in order to penetrate the skull.

The guiding tool may protect the soft tissue during drilling, ensuring that the correct drilling depth is obtained (thus preventing too deep recesses or cavities) and contributing to adequate flushing. In addition, the guiding tool may ensure that the recess or cavity is made perpendicular to the bone and/or skin surface.

The guiding tool or the hollow tube of the guiding tool may comprise an external thread for fixating the guiding tool into the operational site by screwing the guiding tool into the soft tissue.

The thickness of the hollow tube of the guiding tool may vary in order to provide support for the drill bit and also in order to provide room for irrigation or for a coolant inside the hollow tube. The hollow tube of the guiding tool may comprise one upper part comprising a first inner diameter, one lower part comprising a second inner diameter and one middle part located between the upper and the lower part. The inner diameter of the middle part may be variable in order to connect the upper part to the lower part. The first inner diameter may be greater than the second inner diameter. Also, the first inner diameter may be smaller than the second inner diameter.

The guiding tool may comprise a hollow channel connected to the hollow tube in order to provide a coolant or saline to the bottom of the osteotomy. The hollow channel may be arranged essentially perpendicular to the hollow tube for the drill bit. The guiding tool may also comprise a plurality of hollow channels and/or gaps in order to enable the transportation of bone debris out of the guiding tool. The hollow channel and/or the gaps for the bone debris may be located in the upper part of the guiding tool, so that during the drilling process soft tissue does not cover the channels and/or gaps.

The drill bit may comprise a region with an extended diameter which contacts a hard stop of the guiding tool when a predetermined drilling depth is reached. Hereby, idling of the drilling bit can be prohibited when the bottom of the osteotomy is reached.

The guiding tool may be connected to the drill bit, wherein the guiding tool and the drill bit are connected in such a way that the guiding tool is not rotating with the drill bit in order to protect the soft tissue. The guiding tool and the drill bit may also be connected in such a way that that the guiding tool rotates with the drill bit. The drill depth may be controlled by a resilient tube mechanism integrated in the lower part of the hollow tube.

A punch may be integrated into the bottom part of the hollow tube of the guiding tool, so that the incision hole in the bone layer of a skull may be also provided by using the drilling kit.

The drill bit may be connected and/or coupled to the hand piece of the drill through a spring mechanism. When a force is applied to the drill bit, for example when the drill bit is pressed against the skull during drilling, the spring connection may be activated and the hand piece may be enabled to drive the drill bit. When no force is applied to the drill, the spring connection may separate the drill bit from the hand piece and the drill bit stops to rotate. Hereby, a rotation of the drill bit when drilling through the skull bone can be prevented.

The spring mechanism may comprise a spring coupling, wherein the spring coupling may comprise at least two spring elements. The spring elements may be arranged to each other in a horizontal plane or in a vertical plane.

The incision hole may be provided in a soft tissue by pressuring a sharp blade of a cylindrical hollow punch member through the soft tissue. This may be followed by pulling out the cylindrical hollow punch member and removing the punched out soft tissue from the incision hole.

The implantable fixture screw unit may be configured to receive a bone conduction hearing aid system. The implantable fixture screw unit may comprise an elongated part where a first end of the elongated part is threaded and configured to be anchored in the skull bone of the recipient via the drilled cavity or the recess in the skull. The elongated part may comprise a second end configured to receive a skin abutment unit configured to receive the bone conduction hearing aid system. The variation in skin thickness in patients is addressed by the skin abutment unit of different lengths. An outer surface of the elongated part may be modified by laser ablation for the purpose of roughen the outer surface and obtaining an improved osseointegration of the implantable fixture screw unit.

Where an unthreaded part of the elongated part may have a length within a range of 3 mm to 12 mm, 3 mm to 9 mm or 3 mm to 8 mm. The length of the unthreaded part of the elongated part may be orthogonal to the skull. The length may be adapted to the thickness of the soft tissue on the skull of the patient.

The skin abutment unit may have a thickness orthogonal to the skull of between 3 mm to 12 mm, 3 mm to 9 mm or 3 mm to 8 mm.

The skin abutment unit may be attached to the elongated part by screwing it on to the elongated part or by a snap coupling where the skin abutment unit is pressed on to the elongated part by a movement along an axis orthogonal to the skull.

The implantable fixture screw unit may be made of memory metal, such as Nitinol, or an alloy of one or more of following combinations: Ag—Cd, Au—Cd, Cu—Al—Ni, Cu—Sn; Cu—Zn, Cu—Zn—(Si,Sn,Al), In—Ti, Ni—Al, Ni—Ti, Fe—Pt, and Mn—C The skin abutment unit may be formed in one piece with the elongated part.

A diameter of the unthreaded part of the elongated part is smaller than a diameter of the threaded elongated part. The diameter of the unthreaded part of the elongated part is smaller than a diameter of the skin abutment unit.

The unthreaded elongated part may be manufactured from an elastic material, such as NiTi alloy, super-elastic polymer or super elastic ceramics. However, the disadvantages of utilizing such materials are as following:

Forces that are excerted on the elongated part during use or trauma will not be transferred fully to the implant but rather results in bending of the elongated part.

A super-elastic material, such as NiTi alloy, has an e-modulus and stress-strain behavior that is more similar to tissue compared with titanium or steel. Action such as scratching the head, chewing, turning the head and talking will result in movements of the soft tissue around the abutment, generating interfacial stresses around the abutment.

The disadvantages of having a flexible implantable fixture screw unit can be reduced by decreasing the diameter and/or the length of the implantable fixture screw, for example the elongated part. By reducing the diameter of the flexible implantable fixture screw provides another challenge such as how to connect a bone conduction hearing device on to the implantable fixture screw unit.

To solve the problem of reduced diameter the implantable fixture screw unit may include two or more of the elongated parts, where the unthreaded part of the elongated part is made of the elastic material, such as NiTi alloy, super-elastic polymer or super elastic ceramics. In this example, the diameter of the unthreaded part of the elongated part is smaller than a diameter of the threaded elongated part. The diameter of the unthreaded part of the elongated part is smaller than a diameter of the skin abutment unit.

The bone conduction hearing aid system may be configured to be connected to the two or more elongated parts either directly or via an adapter unit. The adapter unit is configured to interconnect the two or more elongated parts on a first surface of the adapter unit and to connect to the bone conduction hearing aid system on a second surface of the adapter unit, and wherein the first surface is opposite to the second surface. Instead of having a skin abutment unit connected to each of the two or more elongated parts, it would be of an advantage to interconnect the two or more elongated parts with the adapter unit and without the skin abutment units being connected to the two or more elongated parts. Thereby, the distance from the skin surface to the bone conduction hearing aid system applied onto the implantable fixture screw unit is reduced.

The shape of the two or more elongated parts may be straight. In another example, the two or more elongated parts may be trapeze shaped or tapered resulting in a smaller diameter at the first end of the elongated part where the skin abutment unit is applied or the adapter unit. The tapered shape and the trapeze shape is beneficial in terms of stability since only a limited part (near the first end) of the elongated part is bending/flexible when subjected to lateral force from the bone conduction hearing aid system.

The elongated part may have a diameter that varies according to a profile along the length, wherein the profile may be a trapeze profile, tapered profile, or an hour-glass profile.

Aforementioned features shall be considered to be disclosed in any combination with each other. Further, the disclosure of any means for performing a method step shall be understood to also disclose the respective method step and the disclosure of a method step shall be understood to also disclose respective means for performing the step.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

Figure 1:
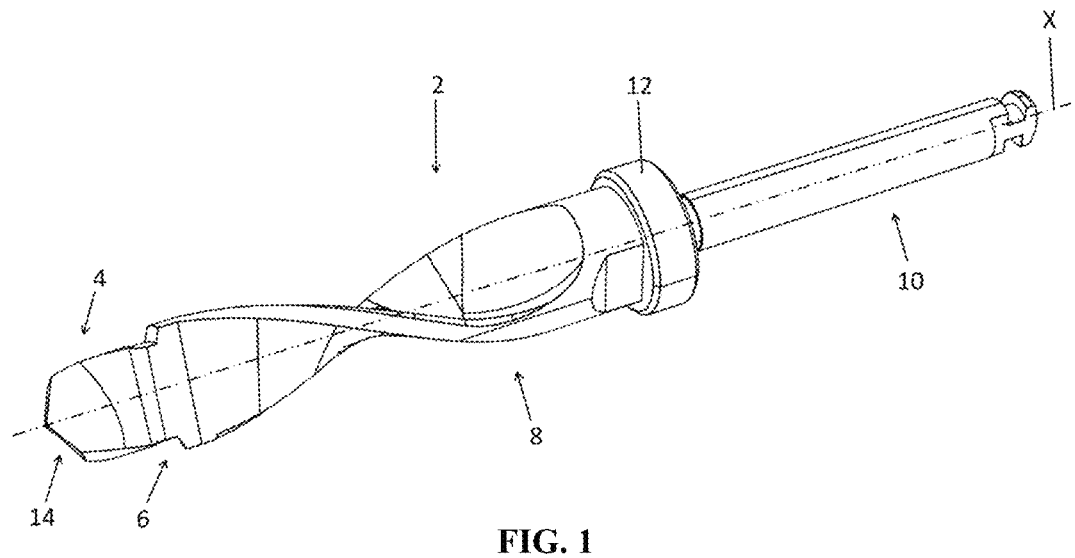
FIG. 1 schematically shows a perspective view of a drilling bit according to an embodiment of the disclosure.

Now referring to FIG. 1, which illustrates a perspective view of a drill bit 2 for drilling a cavity or a recess into a skull according to an embodiment of the disclosure. The drill bit 2 comprises a first part 4, a transition part 6 and a second part 8. The transition part 6 is arranged between the first part 4 and the second part 8. The drill bit 2 comprises a shank 10 in order to connect the drill bit 2 to a hand piece. Between the second part 8 and the shank 10 a circumferential flange 12 is arranged.

The first length of the first part 4 of the drill bit 2 is less than the second length of the second part 8 of the drill bit 2. The length ($l_l$) along the longitudinal axis (X) and between the end of the drill tip (14) and a maximum diameter of the transition part (6) may be between 4.65 mm and 4.75 mm.

Figure 2:
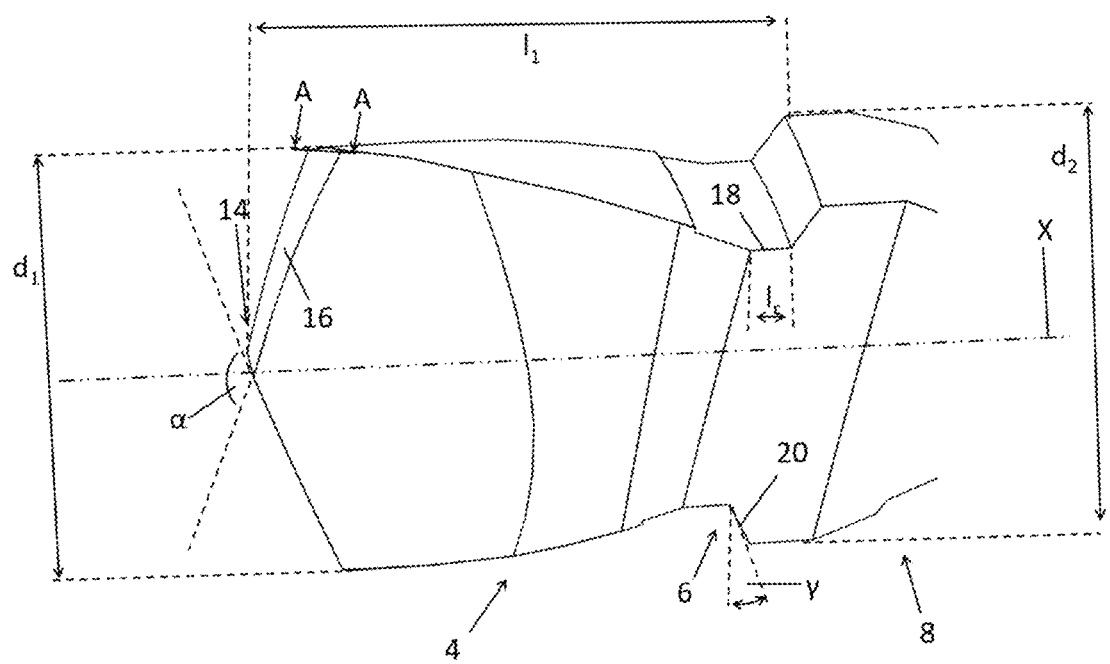
FIG. 2 schematically shows a detail view of the embodiment shown in FIG. 1.

As show in FIG. 2, the first part 4 of the drill bit 2 comprises a drill tip 14 with a tip angle α of between 137 degrees and 143 degrees along a longitudinal axis X of the drill bit 2. The first part 4 of the drill bit 2 is the part of the drill bit 2 which is closest to the bone during drilling.

The first part 4 further comprises a first drill diameter $d_1$, wherein the drill diameter $d_1$ is bordering flanks 16 of the drill tip 14. The drill tip 14 may have a first drill diameter $d_1$ between 3.78 mm and 3.82 mm. The second part 8 may have a second drill diameter $d_2$, wherein the second drill diameter $d_2$ is greater than the first drill diameter $d_1$. By providing a drill bit 2 comprising a first drill diameter $d_1$ and a second drill diameter $d_2$, wherein the second drill diameter $d_2$ is greater than the first drill diameter $d_1$, a cavity or a recess for an implantable fixture screw unit of a hearing aid system may be drilled into the skull in one drill step. Hereby, the final osteotomy for an implant may be performed in one step.

Figure 3:
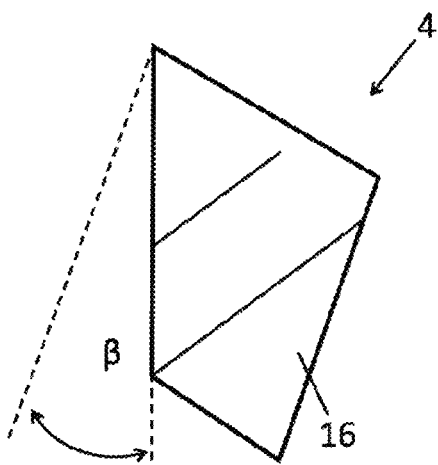
FIG. 3 schematically shows the cross sectional view A-A from FIG. 2.

The first part 4 of the drill bit 2 further comprises a cutting edge angle β. As shown in FIG. 3, the cutting edge angle β may be defined as an angle formed by a flank 16 of the drill tip and a plane perpendicular to the longitudinal axis X. The cutting angle may lie between 7 degrees and 13 degrees.

The drill tip 14 of the drill bit 2 comprises a back rake angle of substantially 0 degrees. The back rake angle of substantially 0 degrees leads to a sharp drill tip 14 whereby cutting forces and power requirements for the drill step may be reduced.

The transition part 6 includes a region 18 with an essentially constant diameter along the longitudinal axis X. The length $l_r$ of the region 18 is between 1.05 mm and 1.55 mm and the region 18 may not comprise a cutting edge. The transition part 6 may further comprise a body clearance 20, wherein the body clearance 20 comprises a transition angle γ of 7 degrees to 13 degrees. The transition angle γ is defined as the angle between a plane perpendicular to the longitudinal axis X of the drill bit 2 and the body clearance 20 of the transition part 6 of the drill bit 2. Aforementioned transition angle γ is beneficial for providing a cavity or a recess in a skull with one drill bit 2 in one drilling step.

Figure 4:
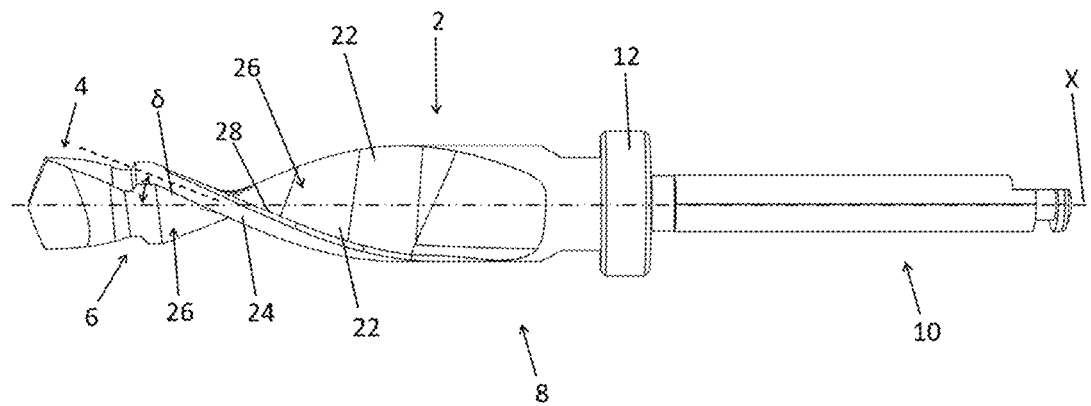
FIG. 4 schematically shows a side view of the embodiment shown in FIG. 1.

FIG. 4 illustrates a side view of the embodiment shown in FIG. 1. As shown in FIG. 4, the second part 8 of the drill bit 2 comprises two flute blades 22 with the second drill diameter dz. Because of the drill diameter $d_2$ being greater than the drill diameter $d_1$ a cavity or a recess for an implantable fixture screw unit of a hearing aid system may be drilled into the skull in one drill step in a beneficial way.

The flute blades 22 each comprise one land 24. The land 24 may be defined as the outer portion of the body of the second part 8 bordering the flute blades 22. Between the two flute blades 22 two flutes 26 are arranged. The opposing surfaces of the flute blades 22 which extend between the lands 24 of the flute blades 22 may comprise a parabolic or an essentially parallel cross-section. The parabolic or essentially parallel surfaces of the flute blades 22 or flutes 26 lead to an improved bone chip extraction. Additionally, the total drill work of the drill bit 2 may be reduced so that an efficient removal of bone volume can be provided.

Each of the flute blades 22 comprises a cutting edge 28. The cutting edge 28 limits the flute land 24 to the cutting side of the flute blades 22. The thickness of the cutting edge 28 may lie between 0.10 mm and 0.40 mm. A cutting edge thickness in the aforementioned range is beneficial for the cutting efficiency of the drill bit 2.

The thickness of the flute blades 22 may vary along the drill bit 2, in particular along the longitudinal axis X of the drill bit 2. This allows for optimizing the thickness distribution of the drill bit 2 regarding the force and torque of the drill bit 2. The thickness of the drill flutes may be between 0.8 mm and 1.2 mm.

The second part 8 of the drill tip 2 includes a helix angle δ of between 24 degrees and 26 degrees, in particular a helix angle δ of essentially 25 degrees, between the longitudinal axis X and a plane of the flute blades 22. Said range of helix angles δ may be beneficial regarding the bone chip removal and the feed rate of the drill bit 2.

Figures 5A, 5B:
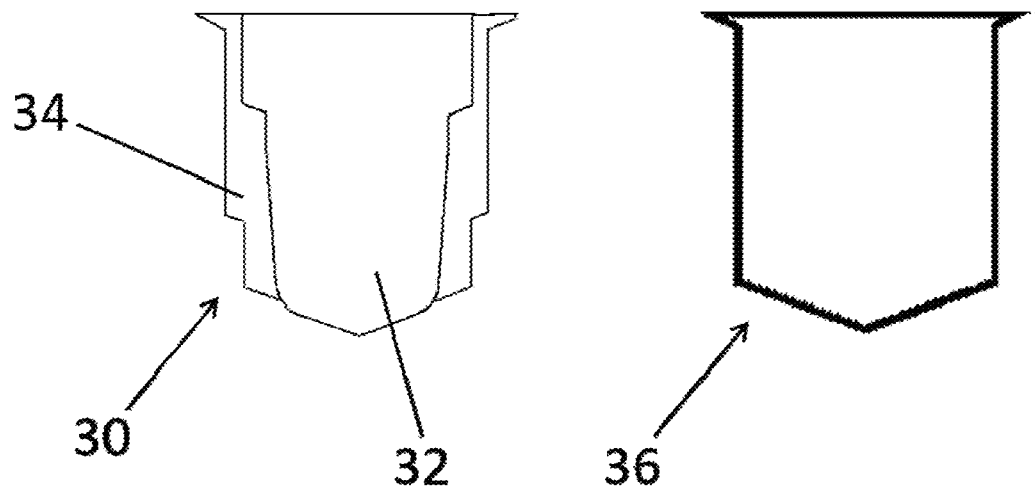
FIG. 5A schematically shows a cavity or a recess drilled with two drill bits according to the state of the art.
FIG. 5B schematically shows a cavity or a recess drilled with one drill bit according to an embodiment of the disclosure.

FIGS. 5A and 5B show a cavity or a recess drilled into a skull in a schematically cross-sectional view. The cavity 30 in FIG. 5A drilled is drilled by two drill bits according to the state of the art. Initially, a first drill is used in order to generate a first cavity 32. Afterwards, a widening drill is used in order to widen the first cavity or recess 32 and to drill a wider cavity 34, thus preparing the cavity or recess 30 for the implant for a bone anchored hearing aid. By using different drills, the operation surgery time is prolonged and the switching, restarting and realigning of the widening drill may cause adverse consequences for the cavity or recess to be drilled. The cavity 36 may be drilled in one step by using the drill bit 2 according to the present disclosure. Hereby, aforementioned disadvantages may be avoided.

Figure 6:
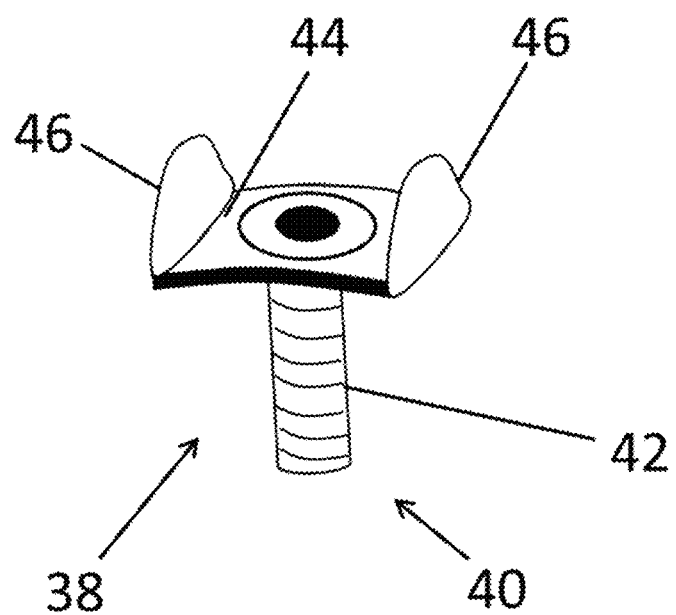
FIG. 6 schematically illustrates a guiding tool according to an embodiment of the disclosure in a perspective view.

FIG. 6 schematically illustrates a guiding tool 38 according to an embodiment of the disclosure in a perspective view. The guiding tool 38 preferably is part of a drill kit comprising the drill bit 2 and the guiding tool 38. The guiding tool 38 may protect the soft tissue during drilling, ensuring that the correct drilling depth is obtained (thus preventing too deep cavities 36) and contributing to adequate flushing. In addition, the guiding tool 38 may ensure that the cavity 36 is made perpendicular to the bone and/or skin surface.

The guiding tool 38 comprises a hollow tube 40 with an external threaded portion 42 for fixating the guiding tool 38 into the operational site by screwing the guiding tool 38 into the soft tissue. The guiding tool 38 further comprises a portion 44 with an enhanced width, wherein the portion 44 with an enhanced width may act as a mechanical stop for the at least on drilling bit 2. The portion 44 is limited by two perpendicular flanges 46 which can be used in order to manipulate the guiding tool 38.

Figure 7:
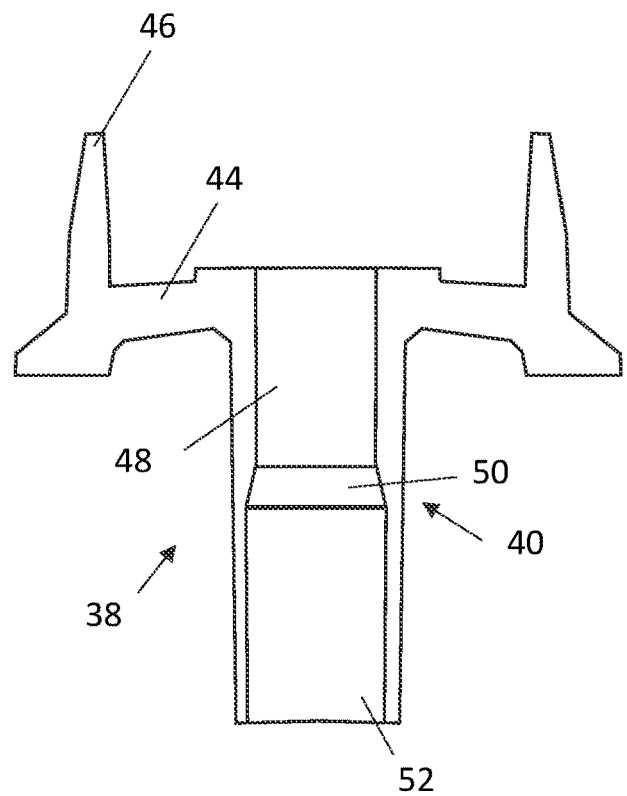
FIG. 7 schematically shows a cross sectional view of a guiding tool according to an embodiment of the disclosure.

The diameter of the hollow tube 40 may vary in order to support the drill bit 2 and to provide space for irrigation room for irrigation or for a coolant inside the hollow tube 40. FIG. 7 schematically shows a cross sectional view of a guiding tool 38 according to an embodiment of the disclosure. The guiding tool 38 has a hollow tube 40 comprising a varying inner diameter. The hollow tube 40 comprises one upper part 48 comprising a first inner diameter, one lower part 52 comprising a second inner diameter and one middle part 50 located between the upper and the lower part. The inner diameter of the middle part 50 is variable in order to connect the upper part 48 to the lower part 52. In the hollow tube 40 shown in FIG. 7, the first inner diameter of the upper part 48 is smaller than the second inner diameter of the lower part 52.

Figure 8:
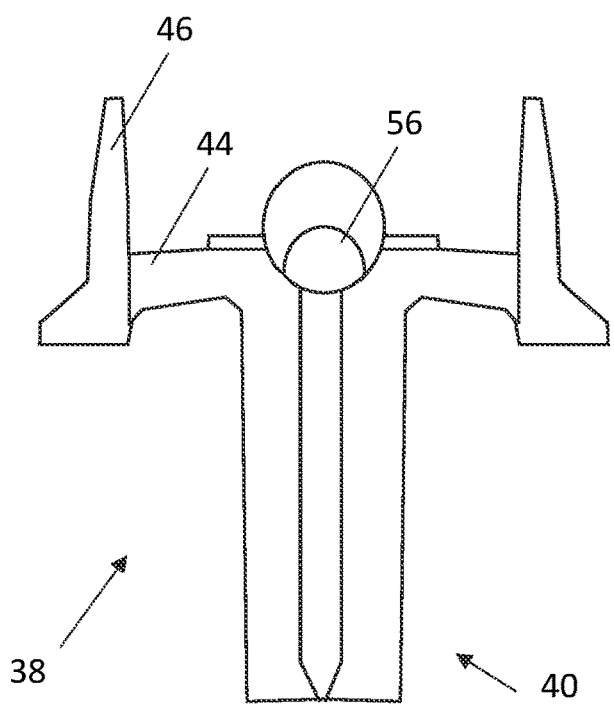
FIG. 8 schematically shows a guiding tool according to an embodiment of the disclosure in a front view.

FIG. 8 schematically shows a guiding tool 38 according to an embodiment of the disclosure in a front view. The guiding tool 38 comprises a hollow channel 56 connected to the hollow tube 40 in order to provide a coolant or saline to the bottom of the osteotomy. The hollow channel 56 may be arranged essentially perpendicular to the hollow tube 40 for the drill bit 2.

Figure 9A:
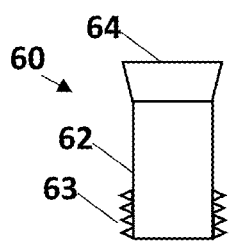
FIGS. 9A-9C illustrate examples of an implantable fixture screw unit.
Figure 9B:
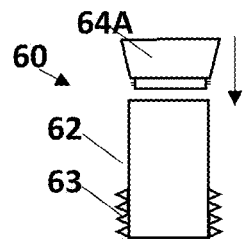
Figure 9C:
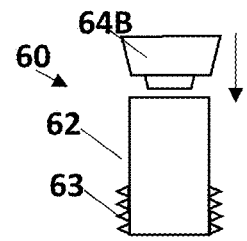

FIGS. 9A, 9B and 9C schematically show an implantable fixture screw unit 60 configured to receive a bone conduction hearing aid system. The implantable fixture screw unit 60 may comprise an elongated part 62 where a first end of the elongated part is threaded 63 and configured to be anchored in the skull bone of the recipient via the drilled cavity or the recess in the skull. The elongated part 62 may comprise a second end configured to receive a skin abutment unit (64, 64A, 64B) configured to receive the bone conduction hearing aid system. The variation in skin thickness in patients is addressed by the skin abutment unit (64, 64A, 64B) of different lengths.

The skin abutment unit 60 may be attached to the elongated part by screwing (64A) it on to the elongated part or by a snap coupling (64B) where the skin abutment unit (64, 64A, 64B) is pressed on to the elongated part 62 by a movement along an axis orthogonal to the skull.

Figure 10A:
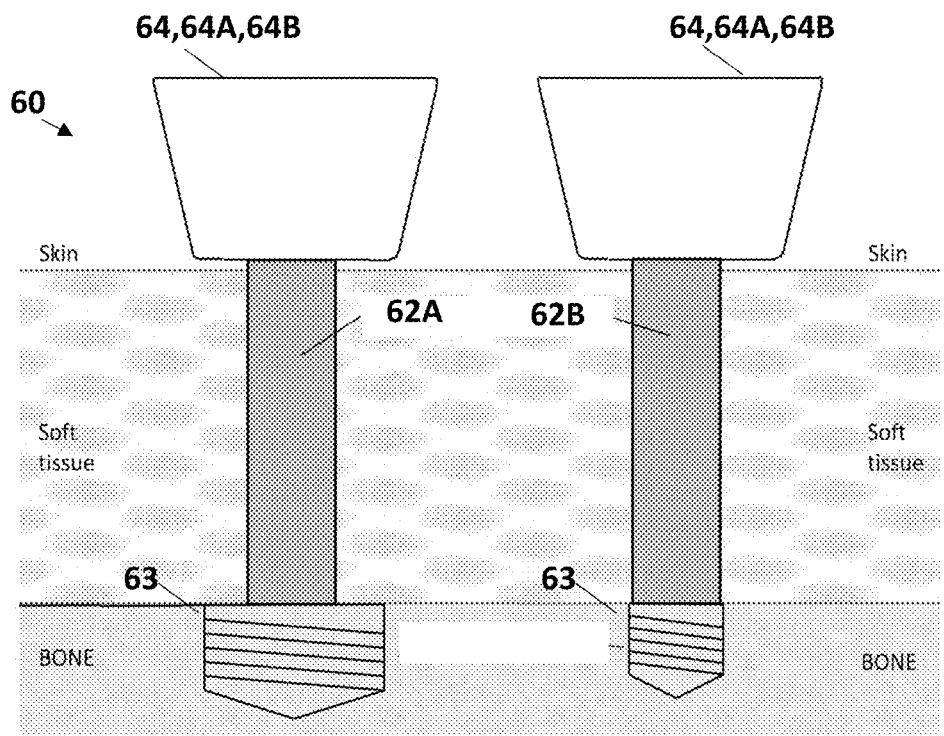
FIGS. 10A-10B illustrate examples of an implantable fixture screw unit.
Figure 10B:
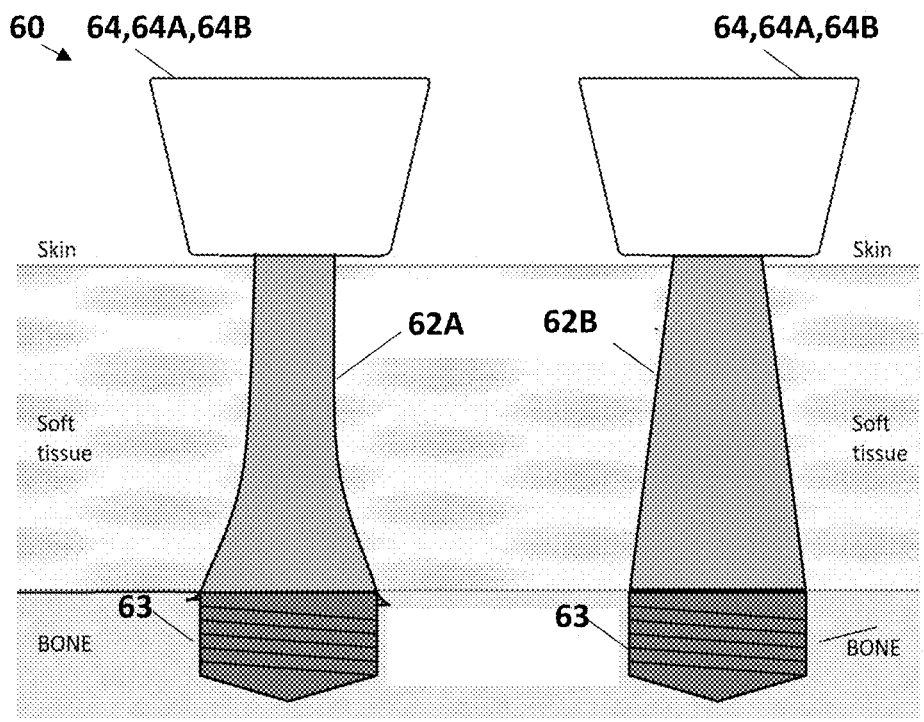

FIGS. 10A and 10B illustrate further examples of the implantable fixture screw unit 60. The implantable fixture screw unit 60 include two or more of the elongated parts (62A, 62B), where the unthreaded part of the elongated part (62A, 62B) is made of an elastic material. In FIG. 10A, the elongated part (62A, 62B) is straight, and in FIG. 10B, the elongated part (62A, 62B) is either trapeze shaped or tapered. In a further example, the two or more elongated parts may be of the same or different shape. In The diameter of the unthreaded part (62A, 62B) is smaller than a diameter of the threaded elongated part 63. The diameter of the unthreaded part (62A, 62B) of the elongated part is smaller than a diameter of the skin abutment unit (64, 64A, 64B).

Figure 11A:
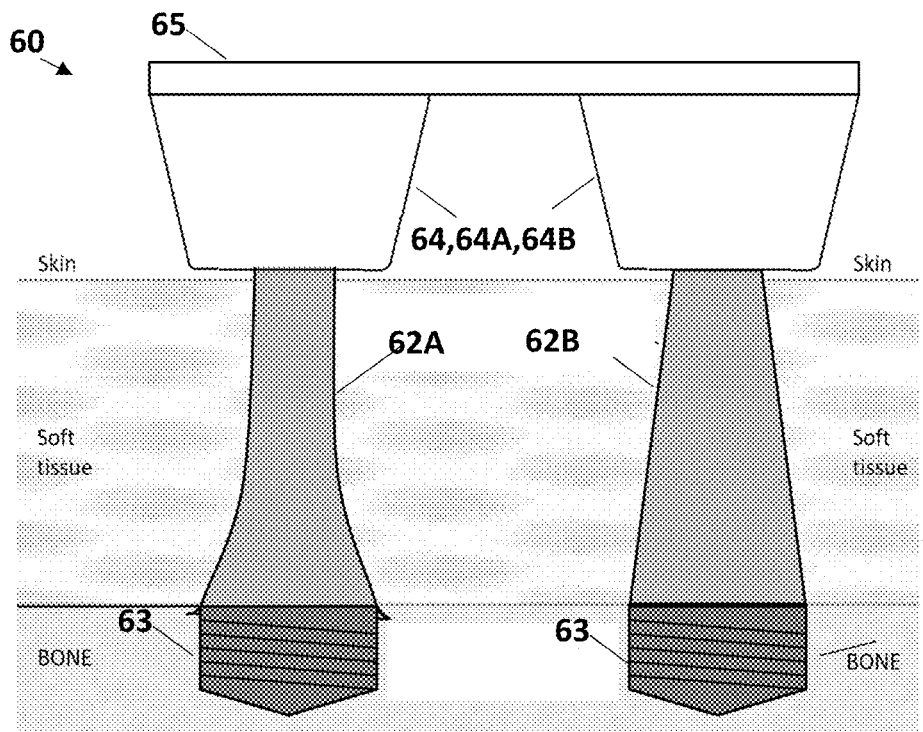
FIGS. 11A-11C illustrate examples of an implantable fixture screw unit and an adapter unit.
Figure 11B:
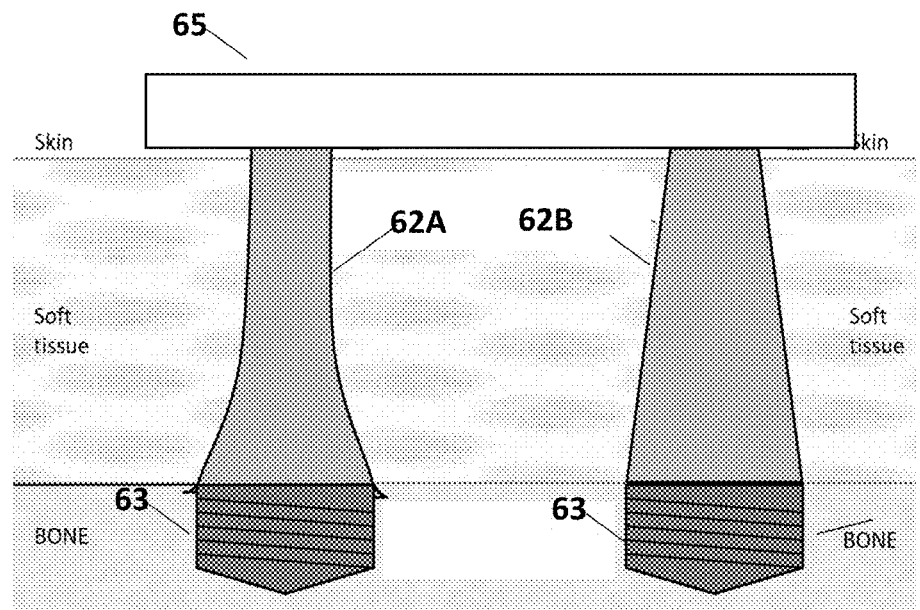
Figure 11C:
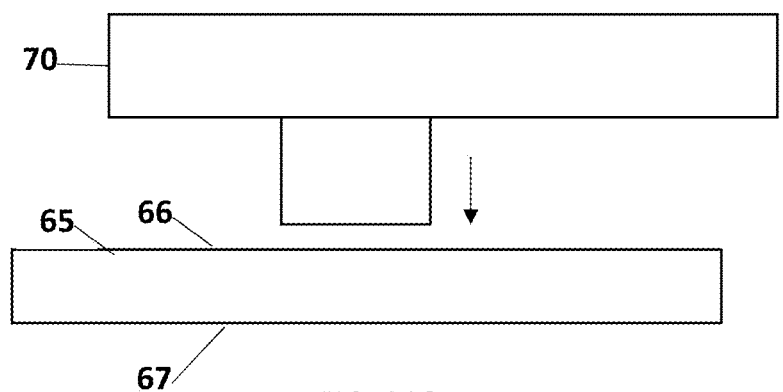

The bone conduction hearing aid system may be configured to be connected to the two or more elongated parts (62A, 62B) either directly onto the skin abutment unit (64,64A,64B) or via an adapter unit 65. FIGS. 11A to 11C illustrate an example of the adapter uniter 65. The adapter unit 65 is configured to interconnect the two or more elongated parts (62A, 62B) on a first surface 67 of the adapter unit 65 and to connect to the bone conduction hearing aid system 70 on a second surface 66 of the adapter unit 65, and wherein the first surface 67 is opposite to the second surface 66, see FIG. 11B. Instead of having a skin abutment unit (64,64A,64B) connected to each of the two or more elongated parts, it would be of an advantage to interconnect the two or more elongated parts (62A, 62B) with the adapter unit 65 and without the skin abutment units being connected to the two or more elongated parts, see FIG. 11B. Thereby, the distance from the skin surface to the bone conduction hearing aid system applied onto the implantable fixture screw unit is reduced.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure.

The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A drill bit for drilling a cavity or a recess into a skull, wherein the cavity or the recess is configured to receive an implantable fixture screw unit of a hearing aid system, the drill bit comprising:
a first part including a drill tip with a first drill diameter, wherein the drill tip comprises a tip angle of between 137 degrees to 143 degrees along a longitudinal axis of the drill bit and wherein the drill tip comprises a back rake angle of between −1 degree and +1 degree,
a second part including a plurality of flute blades with a second drill diameter, wherein the second drill diameter is greater that the first drill diameter, and
a transition part which is arranged between the first part and the second part and along the longitudinal axis, wherein the transition part includes a body clearance.

2. The drill bit according to claim 1, wherein each of the plurality of flute blades of the second part comprises at least one land, and wherein the second part comprises parabolic or essentially parallel opposing surfaces extending between the lands of the plurality of flute blades.

3. The drill bit according to claim 2, wherein the plurality of flute blades comprises a cutting edge with a thickness of between 0.10 mm to 0.40 mm.

4. The drill bit according to claim 2, wherein drill flutes are arranged between adjacent flute blades of the plurality of flute blades and wherein a thickness of the drill flutes varies along the drill bit and/or wherein the thickness of the drill flutes is between 0.8 mm and 1.2 mm.

5. The drill bit according to claim 2, wherein the second part or the transition part includes a back-rake angle which is either positive or negative and/or wherein a back rake angle of the flute blades is within an angle range of between −3 degrees to +3 degrees not including 0 degrees.

6. The drill bit according to claim 1, wherein the plurality of flute blades comprises a cutting edge with a thickness of between 0.10 mm to 0.40 mm.

7. The drill bit according to claim 6, wherein drill flutes are arranged between adjacent flute blades of the plurality of flute blades and wherein a thickness of the drill flutes varies along the drill bit and/or wherein the thickness of the drill flutes is between 0.8 mm and 1.2 mm.

8. The drill bit according to claim 6, wherein the second part or the transition part includes a back-rake angle which is either positive or negative and/or wherein a back rake angle of the flute blades is within an angle range of between −3 degrees to +3 degrees not including 0 degrees.

9. The drill bit according to claim 1, wherein drill flutes are arranged between adjacent flute blades of the plurality of flute blades and wherein a thickness of the drill flutes varies along the drill bit and/or wherein the thickness of the drill flutes is between 0.8 mm and 1.2 mm.

10. The drill bit according to claim 9, wherein the second part or the transition part includes a back-rake angle which is either positive or negative and/or wherein a back rake angle of the flute blades is within an angle range of between −3 degrees to +3 degrees not including 0 degrees.

11. The drill bit according to claim 1, wherein the second part or the transition part includes a back-rake angle which is either positive or negative and/or wherein a back rake angle of the flute blades is within an angle range of between −3 degrees to +3 degrees not including 0 degrees.

12. The drill bit according to claim 1, wherein the second part includes a helix angle between the longitudinal axis and a direction of the flute blades of between 20 degrees and 30 degrees.

13. The drill bit according to claim 12, wherein the helix angle is between 24 degrees to 26 degrees.

14. The drill bit according to claim 1, wherein the transition part includes a region with an essentially constant diameter along the longitudinal axis and/or wherein a length of the region with an essentially constant diameter along the longitudinal axis is between 1.05 mm and 1.55 mm and/or wherein the region with an essentially constant diameter does not have a cutting edge.

15. The drill bit according to claim 1, wherein the body clearance includes a minimum diameter equal to a minimum diameter of the first part and a maximum diameter equal to a diameter of the second part.

16. The drill bit according to claim 1, wherein the body clearance includes a transition angle of 7 degrees to 13 degrees along the longitudinal axis and between a minimum diameter and a maximum diameter of the transition part.

17. The drill bit according to claim 1, wherein a length along the longitudinal axis and between an end of the drill tip and a maximum diameter of the transition part is between 4.65 mm and 4.75 mm.

18. The drill bit according to claim 1, wherein the drill tip has a first drill diameter of between 3.78 mm to 3.82 mm and/or wherein the drill tip comprises a cutting edge angle of between 7 degrees to 13 degrees.

19. A drill kit, comprising a drill bit according to claim 1, wherein the drill kit further comprises a guiding tool, wherein the guiding tool comprises a hollow tube, and wherein a diameter of the hollow tube is greater than the second drill diameter.

20. The drill bit according to claim 1, wherein the back rake angle is substantially 0 degrees.

* * * * *